United States Patent [19]

Strohmaier

[11] Patent Number: 5,454,718
[45] Date of Patent: Oct. 3, 1995

[54] HANDPIECE HEAD FOR A MEDICAL OR DENTAL HANDPIECE WITH A RECIPROCATING TREATMENT TOOL

[75] Inventor: Ernst Strohmaier, Bad Schussenried, Germany

[73] Assignee: Kaltenbach & Voigt GmbH & Co., Biberach/Riss, Germany

[21] Appl. No.: 65,918

[22] Filed: May 25, 1993

[30] Foreign Application Priority Data

Jun. 5, 1992 [DE] Germany .......................... 42 18 683.8

[51] Int. Cl.⁶ .............................. A61C 1/07; A61C 3/03; A61C 3/08
[52] U.S. Cl. .......................................... 433/122; 433/123
[58] Field of Search ................................... 433/114, 118, 433/122, 123, 125, 127

[56] References Cited

U.S. PATENT DOCUMENTS

| | | | |
|---|---|---|---|
| 3,552,022 | 1/1971 | Torbjorn | 32/58 |
| 4,341,519 | 7/1982 | Kuhn et al. | 433/122 |
| 4,536,157 | 8/1985 | Maizenberg | 433/129 |
| 4,629,426 | 12/1986 | Levy | 433/123 X |
| 4,979,899 | 12/1990 | Romhild et al. | 433/122 X |
| 4,984,985 | 1/1991 | Edwardson | 433/123 |
| 5,145,369 | 8/1992 | Lustig et al. | 433/123 X |

FOREIGN PATENT DOCUMENTS

WO9000885  2/1990  WIPO.

*Primary Examiner*—Nicholas D. Lucchesi
*Attorney, Agent, or Firm*—Fitzpatrick, Cella, Harper and Scinto

[57] ABSTRACT

In a handpiece head for a medical or dental handpiece having an in particular angular housing, in which a treatment tool is mounted so that it can move back and forth along it centre axis and rotate, wherein a rotating position adjustment device for the treatment tool is associated with the handpiece head, and has a positioning coupling with two interacting coupling parts, a rotating engagement member for the treatment tool that is manually externally accessible is movably mounted on or in the housing, the rotatable engagement member and/or the positioning coupling are/is connected to the treatment tool by a displacement coupling that enables stroke movement of the treatment tool, and the positioning coupling is effective between the housing and the rotatable engagement member or the treatment tool.

28 Claims, 3 Drawing Sheets

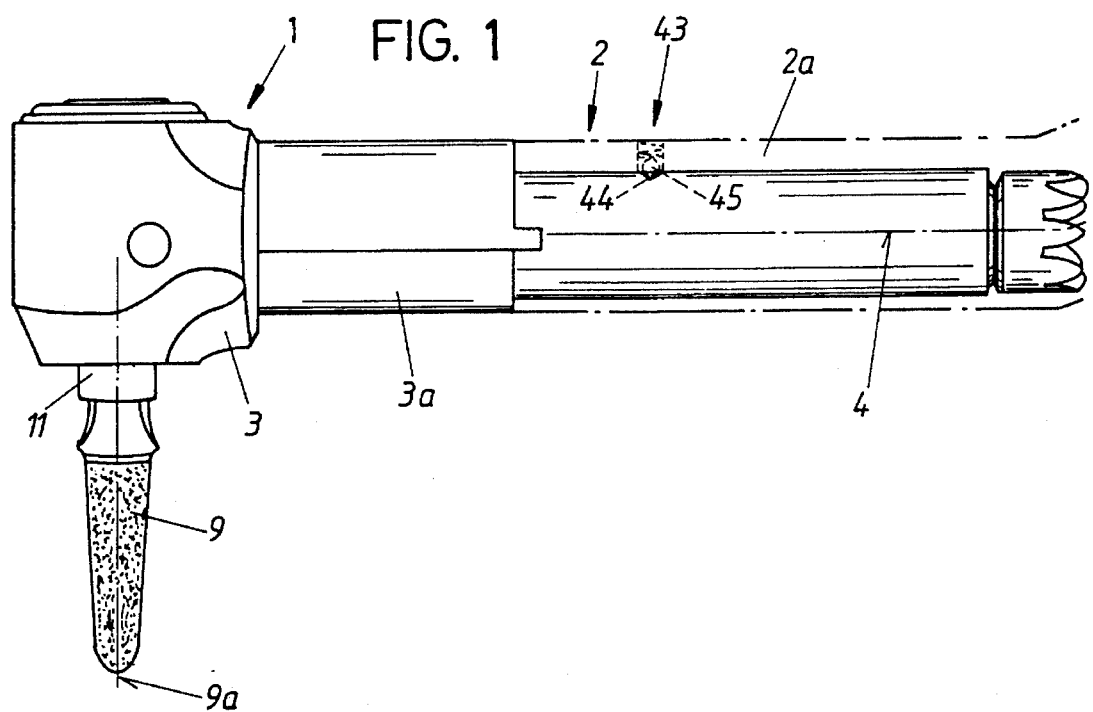
FIG. 1
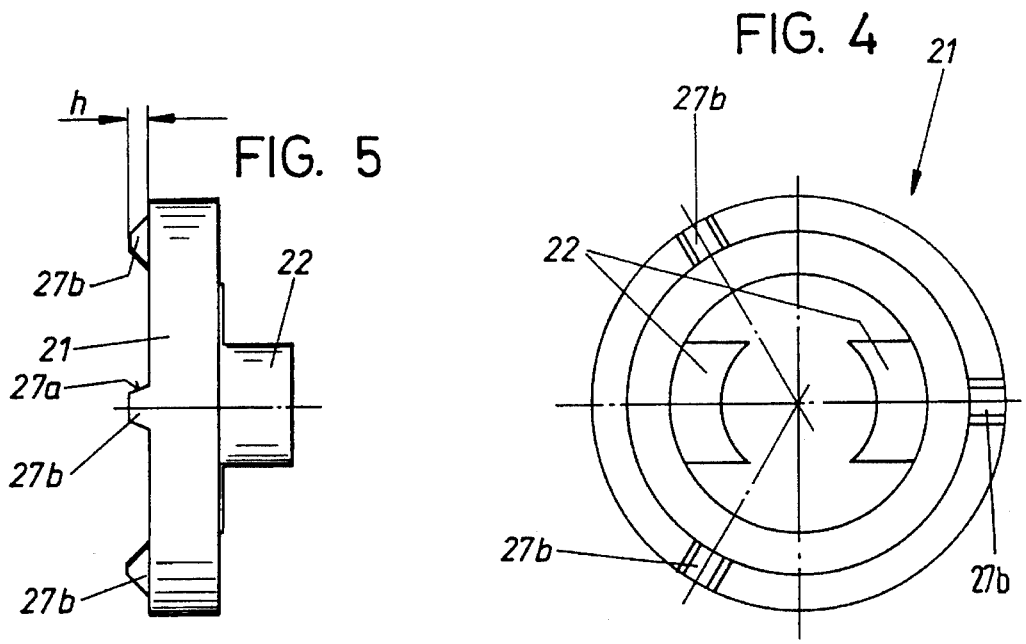
FIG. 5
FIG. 4
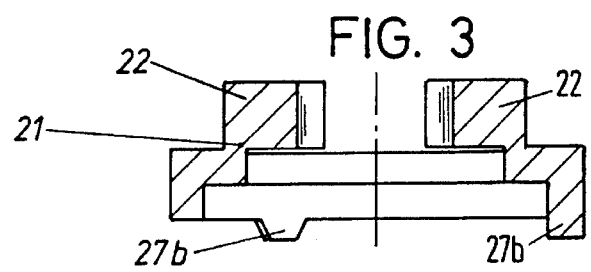
FIG. 3

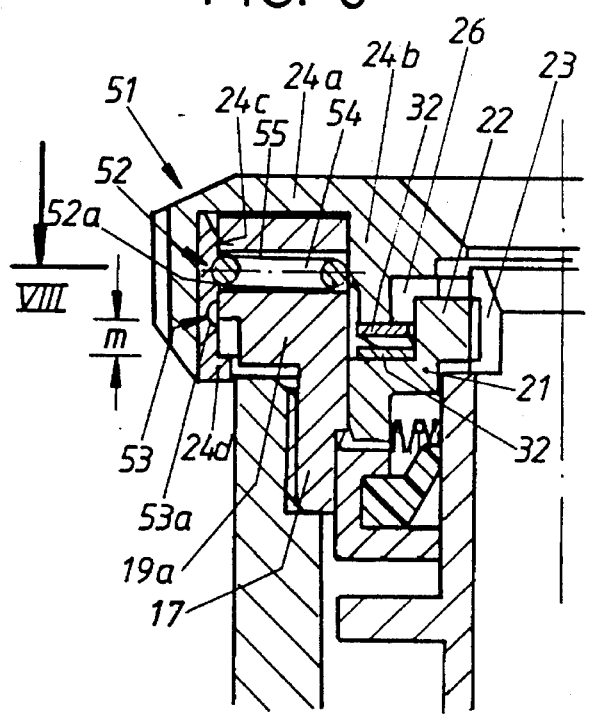
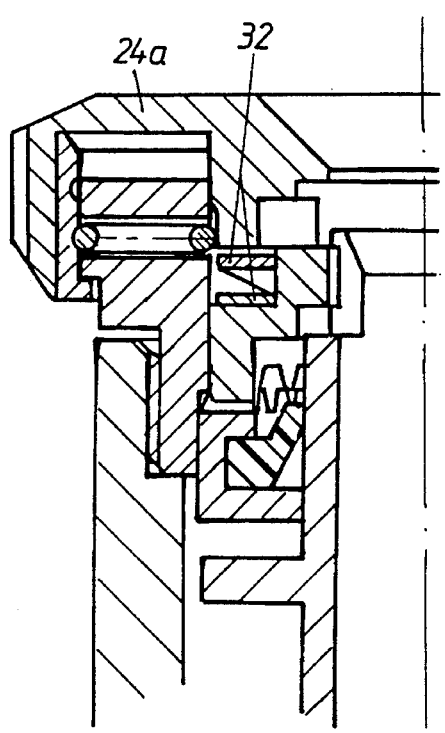
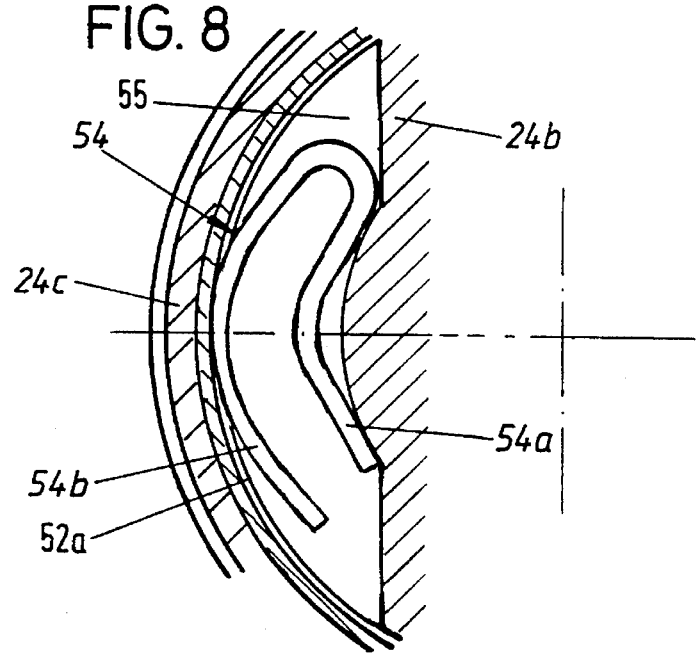

HANDPIECE HEAD FOR A MEDICAL OR DENTAL HANDPIECE WITH A RECIPROCATING TREATMENT TOOL

TECHNICAL FIELD OF THE INVENTION

The invention relates to a handpiece head for a medical or dental handpiece with a reciprocating treatment tool.

BACKGROUND OF THE INVENTION AND PRIOR

In addition to rotating treatment tools there are also reciprocating treatment tools, i.e. treatment tools which carry out a stroke movement, for example having a flat or laminar cross-section. A treatment tool of this kind may be a tool for working on or cleaning teeth.

A handpiece head of this kind is described in U.S. Pat. No. 3,552,022. In this known construction the treatment tool can be clamped into a stroke sleeve that is mounted to be longitudinally displaceable in bearings in the handpiece head and can be displaced longitudinally by an eccentric of a drive shaft which in the present exemplary construction extends as an angular head at right angles to the stroke sleeve. The eccentric engages in a peripheral groove in the stroke sleeve. The stroke sleeve and the treatment tool can thus rotate freely even during operation and therefore with this construction it is only possible to work with the full face of the available, in particular laminar, longitudinally displaceable treatment tool, in particular a flat file. As soon as the person carrying out the treatment turns the handpiece slightly to exert torque on the treatment tool the latter also rotates and therefore specific forming or profiling work cannot be carried out on the tooth simply because the treatment tool always adjusts to lie flat against the surface to be treated.

If a drive connection were to be provided on the treatment tool with which the treatment tool is mounted so that it can move longitudinally but cannot rotate in the handpiece head, torque could indeed be exerted onto the treatment tool with the handpiece and thus specific forming work could be carried out on the tooth or between teeth, but there would then be the danger that with the aforementioned torque a considerable lever effect would be applied to the tooth which could damage it. An example of this would be if a flat file sitting between two teeth were rotated. The flat file would spread the teeth apart due to its rotation and it must be taken into consideration that, owing to the effective lever arm provided by the length of the handpiece, a considerable torque can be conveyed with the treatment tool through which damage could be caused to the tooth.

To avoid the difficulty described above it has been proposed according to WO/90/00885 with a handpiece head of the kind mentioned in the introduction, to limit the torque from the handpiece that can be conveyed by means of the treatment tool to the tooth. According to FIGS. 1, 1A and 2 of this publication an angular handpiece head is provided and the treatment tool has a securing shaft with which it can be inserted from the operating side of the handpiece head into a longitudinally reciprocating stroke sleeve in the handpiece head and in which the securing shaft is positioned in the inserted condition by a form-locking positioning coupling.

There are several positioning coupling positions available, in the form of a plurality of recesses in the lower edge of the stroke sleeve into which a coupling pin at the lower end of the securing shaft of the treatment tool can be introduced as desired by inserting it from below and from which the coupling pin can be withdrawn again by pulling it downwards. With the embodiment shown in FIG. 2 an excessive rotational force (over-turning) protection device in the form of an over-turning coupling (a coupling which releases or is overcome in response to excessive rotational force) is associated with this known handpiece head and comprises one or several axial and groove-shaped recesses distributed around the periphery, and a coupling member in the form of a ball that is arranged in a recess in the inner wall of the housing so that it projects into the interior and thus engages in one of the groove-shaped coupling recesses. The stroke sleeve consists of a plastics material having a certain flexibility or resilience. When torque is conveyed with the handpiece by means of the treatment tool onto the tooth to be treated that is greater than a specific torque, the rib walls between the coupling recesses yield so that the over-turning coupling formed in the manner described above is released or is overcome. Damage to the tooth is hereby intended to be avoided. This known embodiment is disadvantageous for several reasons. The torque by which the over-turning coupling is to be released or overcome cannot be determined exactly, so that different over-turning or release moments arise, depending on the consistency of the material, with which damage to the tooth already occurs. Furthermore it must be anticipated that after over-turning, altered resistance values of the material result, so that slackening of the over-turning coupling must be reckoned with. In addition the positioning coupling can only be operated with difficulty: the treatment tool must be grasped directly by hand, which impairs the sharpness of the treatment tool and is questionable on grounds of hygiene. According to FIGS. 3 to 18 the treatment tool is formed integrally with a securing- and drive shaft. With such a construction the positioning coupling and the over-turning coupling are thus directly effective between the housing and the treatment tool. As shown in FIG. 15 there are not only the coupling recesses of the positioning coupling arranged in the upper region of the securing shaft of the treatment tool but also a single coupling recess is provided in the lower region of the securing shaft in the manner of a longitudinal groove, so that the longitudinal displaceability of the treatment tool is ensured.

OBJECTS OF THE INVENTION

It is an object of the invention to provide a handpiece head for a medical or dental handpiece with a reciprocating treatment tool so that on the one hand functional reliability with the most constant possible over-turning initiating moment is provided and/or on the other hand user-friendly rotational positioning of the treatment tool is possible. Furthermore it is an object of the invention to provide for variation of desired initiating moments of the over-turning coupling and/or positions of the positioning coupling in a user-friendly manner, and thus to provide for adaptation of the handpiece head to different types of treatment or treatment criteria. It should also be possible to lock as desired the over-turning coupling so that large torques may also be produced with the treatment tool if, for example, the treatment requires this.

SUMMARY OF THE INVENTION

According to the present invention there is provided a handpiece head for a medical or dental handpiece having an in particular angular housing, in which a treatment tool is mounted so that it can move back and forth along it centre axis and rotate, wherein a rotational position adjustment device for the treatment tool is associated with the handpiece head, that has a positioning coupling with two interacting coupling parts, wherein a rotatable engagement member for the treatment tool that is manually externally accessible is movably mounted on or in the housing, the positioning coupling is effective between the housing and the rotatable engagement member or the treatment tool, and the rotatable engagement member and/or the positioning coupling are/is connected to the treatment tool by a displacement coupling that enables stroke movement of the treatment tool.

With such a handpiece head a user-friendly rotational position adjustment is ensured, wherein the treatment tool is freed from direct manual contact and thus soiling and hygienic impairment of the tool does not occur when adjusting the rotational position. Furthermore the treatment tool can be adjusted to a desired rotational position without longitudinal displacement thereof and without releasing its drive connection.

According to the present invention there is also provided a handpiece head for a medical or dental handpiece having an in particular angular housing, in which a treatment tool is mounted so that it can move back and forth along it centre axis, wherein the handpiece head has an over-turning protection device that is effective between the housing and the treatment tool, said device comprising an over-turning coupling with two interacting coupling parts of which the one coupling part is connected to the housing and the other is connected to the tool, wherein the over-turning coupling is connected to the treatment tool by a displacement coupling enabling stroke movement of the treatment tool, wherein the two coupling parts are arranged in or on the housing and the coupling part connected to the treatment tool is connected to the treatment tool by the displacement coupling.

With such a handpiece head a functionally reliable over-turning protection device is obtained, with which triggering or release of the over-turning coupling can be both predetermined exactly and effected exactly, even after an extended service life. Hereby not only is an, in particular, laminar treatment tool protected from overloading but the teeth are also protected from overloading, e.g. when in particular, a laminar treatment tool must be passed through a gap between two teeth or when a treatment tool that is caught in a gap must be pulled out.

According to the present invention there is further provided a handpiece head for a medical or dental handpiece having an in particular angular housing, in which a treatment tool is mounted so that it can move back and forth along it centre axis, wherein the handpiece head has an over-turning protection device that is effective between the housing and the treatment tool, said device comprising an over-turning coupling with two interacting coupling parts and wherein a rotational position adjustment device is provided comprising a positioning coupling having two interacting coupling parts, wherein the over-turning coupling and the positioning coupling are formed by one and the same coupling and both coupling parts of the common coupling are parts of the handpiece head.

With such a handpiece head the positioning coupling and the over-turning coupling are formed by one and the same coupling. By this means not only is the manufacturing outlay reduced considerably, which leads to lesser manufacturing costs, but also operation is less complicated and furthermore this embodiment leads to a compact construction because there is only one coupling.

The invention also relates to a handpiece head for a medical or dental handpiece having an in particular angular housing, in which a treatment tool is mounted so that it can move back and forth along it centre axis, wherein associated with the handpiece head is a rotational position adjustment device for the treatment tool that is effective between the housing and the treatment tool, said device comprising a positioning coupling with two interacting coupling parts, and/or wherein the handpiece head has an over-turning protection device that is effective between preferably the housing and the treatment tool, said device comprising an over-turning coupling with two interacting coupling parts, and wherein arranged on the housing is an externally accessible adjustment device for the positioning coupling and/or the over-turning coupling with which the positioning coupling and/or the over-turning coupling can, as desired, be adjusted into an engaged position and a disengaged position, or locked in the engaged position, or with which the engagement-biassing of the positioning coupling and/or the over-turning coupling can be enlarged, reduced or removed completely.

Such a handpiece head enables user-friendly adjustment of the functional criteria of either the positioning coupling or the over-turning coupling (if present), or of both couplings. The engaging or disengaging moment of each coupling and thus the over-turning moment can be adjusted as desired and adapted to respective applicable treatment criteria. It is thereby possible to set the over-turning coupling and/or the positioning coupling out of operation or to lock the over-turning coupling for example be able to convey a large rotating instrument positively on the treatment tool taking into consideration special treatment criteria.

Features are contained in particular embodiments of the invention which offer further advantages in achieving the objects, make it possible to adjust the rotational position in small rotational steps, lead to stable and functionally reliable configurations of long service life and in addition afford compact constructions that are economical to manufacture.

BRIEF DESCRIPTION OF THE DRAWINGS

The invention and further advantages attainable thereby will now be described in more detail with reference to preferred exemplary embodiments shown in the drawings, in which:

FIG. 1 shows, in side elevation, a handpiece head according to the invention;

FIG. 3 shows a carrier part of the handpiece head in a vertical section;

FIG. 4 shows the carrier part viewed from below;

FIG. 5 shows the carrier part in side elevation;

FIG. 6 shows the main part of a modified handpiece head in a vertical longitudinal section and in an enlarged representation in a first operating position;

FIG. 7 shows the handpiece head of FIG. 6 in a second operating position;

FIG. 8 shows the partial section VIII—VIII in FIG. 6.

DETAILED DESCRIPTION OF PREFERRED EMBODIMENTS ACCORDING TO THE INVENTION

Figure 2:
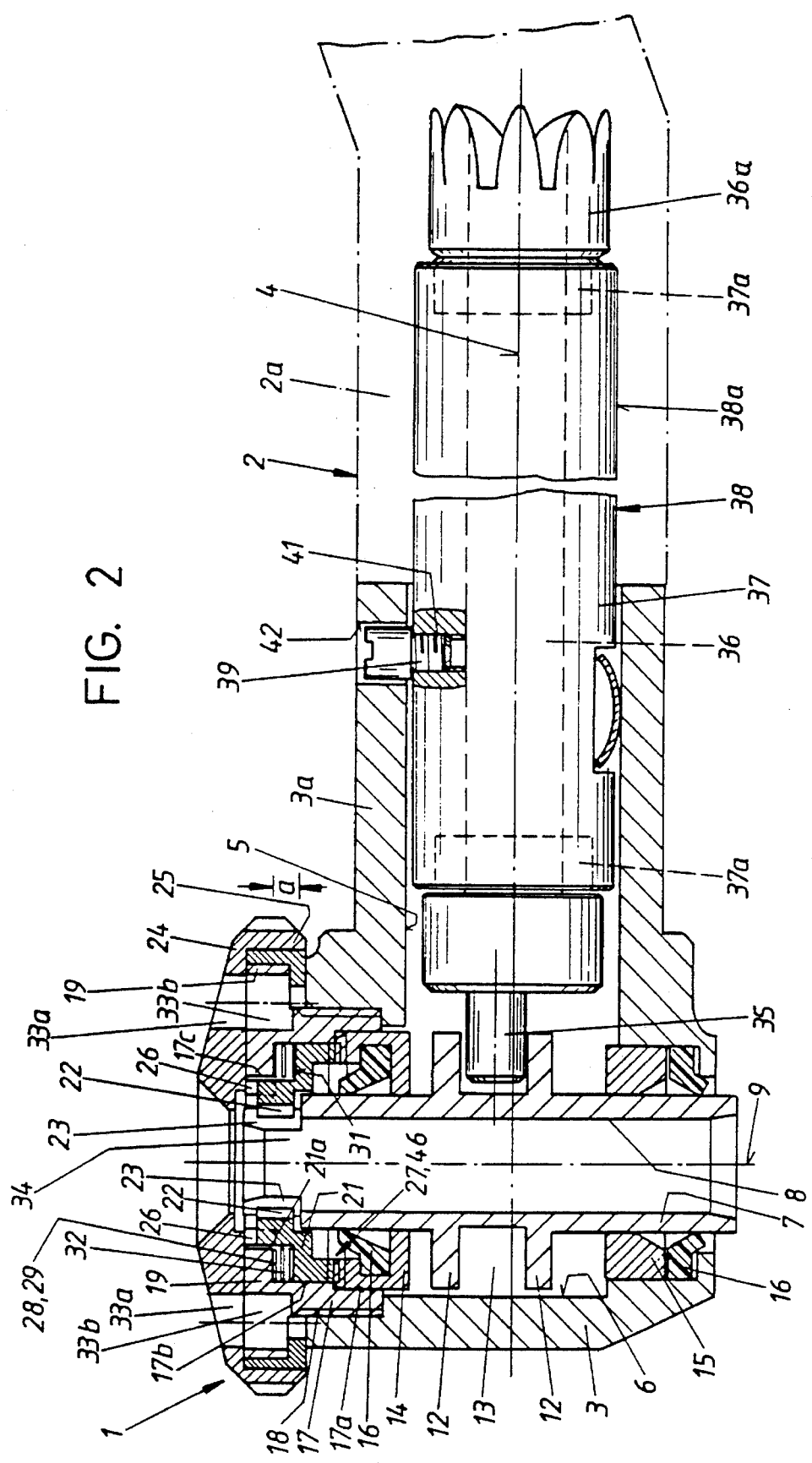
FIG. 2 shows the handpiece head in a vertical longitudinal section and in an enlarged representation.

In the present exemplary embodiment the handpiece head 1 is only part of a handpiece 2 that is only indicated partly in outline. The handpiece head 1 comprises an angular head housing 3 whose rear housing section 3a, when mounted to the handpiece 2, is a forward extension of the gripping sleeve 2a of the handpiece 2 having a longitudinal centre axis 4.

As shown in particular in FIG. 2 the angular head housing 3 has in the region of its housing section 3a an axial bearing bore 5 which leads forward into a continuous bearing bore 6 that extends at right angles thereto and is manufactured with steps. In the bearing bore 6 a hollow cylindrical ram sleeve 7 is mounted so that it can move back and forth a few millimeters in its longitudinal direction, i.e. transverse to the handpiece head 1, and rotate. In the cylindrical bore 8 of the ram sleeve 7 there is a treatment tool 9, shown in FIG. 1, having a cylindrical holding shaft 11 arranged along its centre axis 9a which can be inserted slidingly from the tool side and clamped. The tool 9 operates by oscillating longitudinally and in the present exemplary embodiment it is a cross-sectionally flat or sword-shaped tool 9 in the fashion of a file of which, with its stroke movement, the wide and/or narrow sides can be used for filing or—depending on the fineness—for smoothing or polishing.

The ram sleeve 7 has in its middle region two flanges 12 spaced axially from one another between which a peripheral groove 13 of rectangular cross-section is formed. In its end regions on either side of the flanges 12, the ram sleeve 7 is mounted in sliding bearing rings 14, 15 that are arranged in the region of the bearing bore sections present on both sides, and on the outside of each sliding bearing ring 14, 15 there is a respective sealing ring 16 with a stripper lip directed axially outwards.

The sliding bearing remote from the tool is arranged with its sliding bearing ring 14 in a bush 17 that is screwed (thread 18) into an external step-shaped, enlarged end section of the bearing bore 6. The bush 17 also has a three-stepped bore with an inner bore section 17a in which the sliding bearing ring 14 is inserted securely, a middle bore section 17b in which a carrier ring 21 is mounted rotatably with play for movement, and an outer bore section 17c. The carrier ring 21 has a Z-shaped cross-section and formed integrally on the outer, tapered ring section 21a on the inside are diametrically opposed carrier pins 22 which engage with little play for movement in diametrically opposed radial slits 23 in the ram sleeve 7. The slits 23 lead out to the ends axially.

By this means a first coupling is provided between the ram sleeve 7 and the carrier ring 21 or the flange 19 or the housing 9 which allows longitudinal movement of the ram sleeve 7 necessary for the stroke but prevents the ram sleeve 7 from rotating. The coupling pin or pins 22 and the slits 23 may be arranged inversely.

A rotatable flange 24 is rotatably mounted with little freedom of movement on the flange 19 and is arranged axially on the outside of the flange 19, and with its outer edge 25 overlaps and clasps behind the flange 19 in a C-form whereby the rotatable flange 24 is held on the flange 19 in axial and radial directions, rotatably. On the outer periphery the rotatable flange 24 has ridges, ribs or a knurl to improve its graspability. In the inner wall of the rotating flange 24 or of the flange 19 diametrically opposed axial and radial slits 26 are provided in which the axially projecting carrier pins 22 engage with their radial outer regions with little freedom of movement.

The sliding bearing ring 14 and the carrier ring 21 lie with end faces opposite one another and they engage with one another by means of teeth 27 arranged on each of the end faces. The teeth provided are such that by rotating one part relative to the other part the engagement can be overcome. This is made possible by providing the teeth 27 with oblique flanks 27a, the inclination of the oblique flanks (see FIG. 5) being adapted to the maximum torque that the teeth 27 should convey, so that if this torque is exceeded, the carrier ring 21 is pushed axially outwards out of the teeth engagement. For this purpose clearance for axial movement is provided for the carrier ring 21 between the sliding bearing ring 14 and the inner stepped face 28 of the bush 17. This movement clearance 29 is bounded axially by the stepped face 28 of the bush 17 and the stepped face 31 of the carrier ring 21. The distance a therebetween is larger than the height h of the teeth 27 and the height of one or more zigzag springs 32 arranged in the movement clearance 29 which elastically bias the carrier ring 21 axially into teeth engagement.

Provided in the rotating flange 24 and in the flange 19 are two diametrically opposed axial bores 33a, 33b that can be aligned with one another. The pins of a screw wrench (not shown) can be inserted through the outer bores 33a in the rotating flange 24 into the bores 33b for the purpose of screwing or unscrewing the bush 17. The flange 19 and the rotatable flange 24 are joined together securely and thus form a common rotatable part.

In the present embodiment the rotatable flange 24 has a coaxial hole 34 that can serve to supply cooling- or rinsing liquids to the treatment tool through the ram sleeve 7 by means of a supply device (not shown).

To allow the axial stroke movement of the ram sleeve 7, clearance is needed on either side of the flange 12 as are correspondingly long slits 23 so that the inner carrier pins 22 do not strike against the inner slit ends.

To drive the ram sleeve 7 an eccentric cylindrical driving pin 35 is provided at the front end of the drive shaft train of the handpiece 2, which pin engages in the peripheral groove 13 with little freedom of movement. A drive shaft section 36 is provided in the present exemplary embodiment which carries the drive pin 35, has a toothed coupling or a bevel wheel 36a of a bevel gear on its rear end, and is mounted rotatably in a bearing sleeve 37, preferably in sliding bearings 37a, by which a drive cartridge 38 is formed. The drive cartridge 38 sits in the bearing bore 5 and is secured by a securing screw 39 that is screwed therein radially. The screw 39 is screwed into a radial threaded hole 41 in the bearing sleeve 37 and into a hole 42 in the housing section 3a aligned with the sleeve 37. The bearing sleeve 37 projects beyond the housing section 3a to the rear and forms with this rearward section a bearing journal 38a that can be secured detachably by an elastic detent connection 43 in the handpiece 2, which connection can be overcome by pulling out of the handpiece 2. The detent connection 43 may be formed by at least one detent recess 44 in the outer surface of the bearing journal 38a and a detent sphere 45 that is mounted to move radially in the sleeve of the handpiece 2 and is biassed elastically in the detent recess 44 by a spring (not shown).

In the handpiece head 1 described above rotational positions of the tool 9 can be adjusted as desired relative to the handpiece head 1, independently of the stroke position of the ram sleeve 7 or its drive. The rotational adjustment can be effected in small steps, which is provided for by the relatively small divisions between the teeth 27. The teeth 27 form a second disengageable coupling 46 between the ram sleeve 7 or the carrier ring 21 and the sliding bearing ring 14 which opens automatically when a predetermined torque is exceeded and closes again automatically. By this means it is possible to adjust the tool 9 into a desired rotational position by rotating the rotatable flange 24 in one or the other direction of rotation. If on the other hand a predetermined torque is exceeded at the tool 9, the ram sleeve 7 follows this torque loading automatically and the engagement of the teeth 27 is overcome, being forced through or turned through, i.e. in the manner of a ratchet mechanism turning in its non-locking direction. By this means pressure loading on or damage to the teeth, due to the lever effect resulting when handling the handpiece, is eliminated.

It is not necessary for the teeth 27 to be complete on both teeth parts. The function is ensured even if a complete toothed ring is provided on one part and theoretically only one, preferably two or more teeth 27b are distributed around the periphery of the other part. In the present embodiment three teeth 27b are distributed uniformly, preferably on the carrier ring 21 as shown in FIG. 4. On the sliding bearing ring 14, however, a complete toothed ring is provided with corresponding teeth having oblique flanks.

Depending on the type of dental treatment it may be advantageous to work with a tool 9 that cannot rotate until a predeterminable torque is exercised or cannot rotate beyond this torque, or to work with a tool that is easily or freely rotatable about is longitudinal centre axis. This is made possible with the embodiment shown in FIGS. 6 to 8 in which the same or comparable parts have been provided with the same reference numerals and in which an adjustment device 51 is associated with the handpiece head 1. In the one adjustment position of the adjustment device 51, shown in FIG. 6, the coupling 46 is engaged and thus the tool 9 is, subject to limits, non-rotatable. In the other adjustment position of the adjustment device, shown in FIG. 7, the engagement-biassing of the coupling 46 is reduced or released completely and thus the tool 9 can rotate easily or freely. It is also possible to provide the adjustment device 51 with a further adjustment position in which the torque, at which the coupling 46 can be overcome or over-turned, is very large or at which the coupling 46 cannot be overcome or over-turned.

The adjustment device 51 includes, as shown in FIGS. 6 to 8, an adjustment member with which the one coupling part (here the coupling connected non-rotatably to the ram sleeve 7) can be disengaged and secured in the disengaged position (not shown) or with which the engagement-biassing of the coupling 46 can be reduced or released completely. In the present embodiment, the flange 19 and the rotating flange 24 are affected by modifications in design involving the adjustment device 51. These parts are supplemented in the embodiment shown in FIGS. 6 to 8 with the reference a. In this modification the flange 19a does not have an inner flange at its outer end, rather its inner wall is substantially cylindrical. On the other hand, the rotating flange 24a has a coaxial inner annular projection 24b against the inner face of which the axial springs, here zigzag springs 32, bear which urge the carrier ring 21 with its teeth into the engaged position of the coupling. Furthermore the rotating flange 24a is axially displaceable relative to the flange 19a, and in the pushed-in position shown in FIG. 6 the zigzag springs are compressed axially thus creating engagement biassing which may or may not be overcomable, in accordance with the exemplary embodiment shown in FIGS. 1 to 5. In the position shown in FIG. 7 in which the rotating flange 24a is moved axially outwards relative to the position shown in FIG. 6, the engagement biassing of the coupling, here the zigzag springs 32, is reduced or slackened so that the ram sleeve 7 with the tool 9 can be easily rotated. It is possible to provide a further adjustment position for the rotatable flange 44a in which it is pushed inwards beyond the position shown in FIG. 6, and in which the springs 32 and the teeth 27 are pressed together to such an extent that the movable toothed or coupling part 21 cannot yield and therefore the coupling 46 cannot be overcome or over-turned.

The displaceability of the rotating flange 24a on the flange 19a is made possible by an axial sliding bearing. In the present embodiment the rotating flange 24a overlaps the flange 19a with a hollow cylindrical annular wall 24c that is longer than the effective flange 19a of the bush 17 by the amount of axial displacement m, and the annular wall 24c has at its inner end an inner shoulder 24d which bounds displacement outwards by striking against the flange 19a. The rotating flange 24 can thus slide axially with little freedom of movement on the periphery of the flange 19a. In the coupling position (FIG. 6) and in the quasi end coupling position (FIG. 7) the adjustment device 51 is associated with a respective elastic locking device 52, 53, which can be overcome, to avoid unintentional displacement from the respective adjustment position. In the present embodiment a common resilient element is associated with both locking devices 52, 53 that is arranged on the stationary part, here the flange 19a, and can engage in detent recesses 52a, 53a in the inner wall portion of the annular wall 24c. The resilient element 54 may be a spring wire, as shown in FIG. 8, that is preferably circular in cross-section, U-shaped and curved slightly in the circumferential direction, and is accommodated in a substantially secant slit 55 in the flange 19a, and is supported with its inner limb 54a on the inner annular projection 24b and can engage with its convex outer limb 54b in the detent recesses 52a, 53a that are preferably formed by annular, cross-sectionally rounded detent grooves in the inner wall portion of the annular wall 24c. As in the first exemplary embodiment shown in FIGS. 1 to 5, the inner wall portion of the hollow cylindrical annular wall 24c in the second exemplary embodiment shown in FIGS. 6 to 8 is formed by a thin sleeve with the inner shoulder 24d that sits securely in the annular wall 24c, e.g. is press-fitted.

The adjustment device 51 described above is characterised by a simple, functionally reliable and user-friendly construction. For adjustment between the engaged coupling position shown in FIG. 6 and the quasi end coupling position shown in FIG. 7, the user only needs to grasp the periphery of the rotating flange 24a and move it axially into the respective adjustment position or into the respective locking device 52 or 53. Furthermore the handpiece head 1 may correspond to the embodiment shown in FIGS. 1 to 5. The adjustment device 51 according to the invention is, however, not restricted to a coupling 46 shown in FIGS. 1 to 5. Within the scope of the invention it is possible to associate the adjustment device 51 with another coupling between the tool holder, here the ram sleeve 7, and the housing 3 or a component thereof.

The handpiece head 1 is advantageous with regard to several aspects of the invention. One aspect consists in providing it with a functionally reliable excessive rotation (over-turning) protection device through which damage to the tooth to be treated and also to the treatment tool 9 can be avoided. With such an embodiment of the handpiece head 1, a rotating engagement member for the treatment tool 9, here the rotating flange 24, can be dispensed with or a rotating position adjustment device of another design may be provided.

A second aspect of the invention consists in providing the handpiece head with a user-friendly rotating position adjustment device for the treatment tool 9. In this embodiment an over-turning protection device could be dispensed with (insofar as it is not desired), or an over-turning protection device of another kind could be provided.

According to a third aspect of the invention, the positioning coupling and the over-turning coupling are formed by one and the same coupling, and the coupling can be of a suitable construction.

A fourth aspect of the invention relates to the presence of the adjustment device 51 for the adjustment position setting device or positioning coupling and/or the over-turning protection device or over-turning coupling. With such a handpiece head according to the invention the positioning adjustment device and/or the over-turning protection device can be dispensed with or these couplings may have a different design.

What is claimed is:

1. A medical or dental handpiece comprising
   a housing in which a tool accommodating part and a treatment tool is mounted to move back and forth along, and to rotate about its center axis,
   a rotational position adjustment device, including an over-turning coupling, for the treatment tool mounted in association with the handpiece,
   a positioning coupling which includes two interacting coupling parts, one of which is movable,
   a rotatable engagement member for the treatment tool, said engagement member being manually externally accessible and being movably mounted in the housing,
   the positioning coupling being arranged to couple the rotational position adjustment device and the rotatable engagement member,
   and the rotatable engagement member being connected to the treatment tool by a displacement coupling that enables stroke movement of the treatment tool.

2. A handpiece according to claim 1, wherein the positioning coupling is arranged in the housing.

3. A medical or dental handpiece comprising
   a housing,
   a treatment tool mounted in said housing via a tool accommodating part so that it can move back and forth along its center axis,
   an over-turning protection device including a rotational engagement member arranged between the housing and the treatment tool,
   said protection device comprising an over-turning coupling with two interacting coupling parts of which one coupling part is connected to the housing and the other coupling part is movable and is connected to the tool,
   the over-turning coupling being connected to the treatment tool via a positioning coupling and a treatment tool displacement stroke enabling coupling,
   the two coupling parts being arranged in the housing and the interacting coupling part connected to the treatment tool being connected to the treatment tool via the displacement stroke enabling coupling.

4. A handpiece according to claim 1, or 3 wherein one of said coupling parts is moveable and is connected to one of said treatment tool and said tool accommodating part by said displacement coupling.

5. A medical or dental handpiece comprising
   a housing including a handpiece head,
   a treatment tool mounted in the housing via a tool accommodating part so that it can move back and forth along its center axis,
   an over-turning protection device, including a rotational engagement member, arranged to interconnect the housing and the treatment tool, said overturning protection device comprising an over-turning coupling with two interacting coupling parts, one of which is moveable, and each of which is part of the handpiece head
   said two interacting coupling parts of said over-turning protection device over-turning coupling being arranged to provide rotational position adjustment for said treatment tool.

6. A handpiece according to claim 5, wherein one of said coupling parts is moveable and is connected to one of said treatment tool and a tool accommodating part by a displacement stroke enabling coupling.

7. A handpiece according to claim 3 or 5, wherein the treatment tool is removably secured in a tool accommodating part that is mounted to move back and forth in the handpiece head in the direction of the centre axis of the tool, and is connected to the tool accommodating part by said displacement coupling.

8. A handpiece according to claim 1, 3, or 5 wherein said two interacting coupling parts become disengaged when a predetermined torque imposed on the tool is exceeded.

9. A handpiece according to claim 1, 3 or 5, wherein one of said coupling part is mounted movably in a guide and is urged into its engagement position by spring force.

10. A handpiece according to claim 1, 3 or 5 wherein the coupling parts each have at least one coupling recess and at least one coupling pin which engage with one another.

11. A handpiece according to claim 10, wherein the interacting coupling parts have surfaces formed by teeth between the coupling recesses and coupling pins, said teeth being arranged obliquely.

12. A handpiece according to claim 1, 3 or 5, wherein the direction of movement of the movable coupling part is directed along the centre axis of the treatment tool.

13. A handpiece according to claim 1, 3, or 5 wherein said two interacting coupling parts are arranged concentrically with the center axis of the treatment tool.

14. A handpiece according to claim 1, 3 or 5 wherein said interacting coupling parts are annular parts arranged axially side by side and mounted so that they can be brought into engagement with one another at their sides facing one another, one annular coupling part being arranged on a side remote from the treatment tool being movable whereby there is formed a displacement coupling.

15. A handpiece head according to claim 14, wherein the treatment tool is removably secured in a tool accommodating part that is mounted to move back and forth in the handpiece head in the direction of the center axis of the tool, and is connected to the tool accommodating part by said displacement coupling.

16. A handpiece according to claim 1, 3 or 5 wherein at least one of said two interacting coupling parts is arranged on the tool side in an end region of at least one of the tool and the tool accommodating part.

17. A handpiece according to claim 1, 3 or 5, wherein the rotatable engagement member is accessible from a side of the handpiece head remote from the tool, and is arranged on this side coaxially with the tool.

18. A handpiece according to claim 1, 3 or 5, wherein the rotatable engagement member is formed by one of a disc, a wheel and a rotatable crown.

19. A handpiece according to claim 1, 3 or 5, wherein a bearing, remote from the tool, for the tool accommodating part is arranged in a bush that is inserted into the housing.

20. A handpiece according to claim 19, wherein the rotatable engagement member is mounted rotatably on a flange of the bush towards the end thereof.

21. A handpiece according to claim 20 wherein the one of said two interacting coupling parts is connected between the tool accommodating part and at least one of the housing head, the bush and a bearing ring.

22. A medical or dental handpiece comprising a housing, a treatment tool mounted in the housing so that it can move back and forth along a centre axis thereof, a rotational positional adjustment device for the treatment tool connected between the housing and the treatment tool, said adjustment device comprising a positioning coupling having two interacting parts, and an externally accessible adjustment device arranged on the housing for the positioning coupling and with which the positioning coupling can, as desired, be adjusted into an engaged position and a disengaged position, locked in the engaged position, or with which the engagement-biassing of the positioning coupling can, be enlarged, reduced or removed completely.

23. A handpiece according to claim 22, wherein the adjustment member is a disc that sits on a flange that which is screwed into the housing and is axially displaceable thereon.

24. A medical or dental handpiece comprising a housing, a treatment tool mounted in the housing so that it can move back and forth along a centre axis thereof, an overturning protection device arranged between the housing and the treatment tool, said over-turning protection device comprising an over-turning coupling having two interacting coupling parts, and an externally accessible adjustment device arranged on the housing for the over-turning coupling with which the over-turning coupling can, as desired, be adjusted into an engaged position and a disengaged position, locked in the engaged position, or with which the engagement-biassing of the over-turning coupling can, alternatively, be enlarged, reduced or removed completely.

25. A handpiece according to claim 20 or 24, wherein the adjustment device is accessible from the side remote from the tool and is arranged coaxially with the centre axis of the tool.

26. A handpiece according to claim 20 or 24, wherein the adjustment device has an axially displaceable adjustment member in operative connection with an associated coupling part.

27. A handpiece according to claim 26, wherein for detachably securing the adjustment member in its adjustment positions, releasable locking devices having spring elements engaging resiliently in detent recesses, are arranged on said adjustment member.

28. A handpiece head according to claim 1, 3, 4, 22 or 24, wherein the rotatable engagement member and the adjustment member are formed by one and the same rotating part.

* * * * *